(12) United States Patent
Casavant et al.

(10) Patent No.: US 7,236,828 B2
(45) Date of Patent: Jun. 26, 2007

(54) IMPLANTABLE CARDIOVERTER DEFIBRILLATOR WITH AUTOMATICALLY ADAPTABLE SENSING CONFIGURATION

(75) Inventors: David A. Casavant, Reading, MA (US); Robert F. Collins, Danville, NH (US); Mark L Brown, North Oaks, MN (US); Bruce D. Gunderson, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 308 days.

(21) Appl. No.: 11/096,509

(22) Filed: Mar. 31, 2005

(65) Prior Publication Data

US 2006/0224194 A1 Oct. 5, 2006

(51) Int. Cl.
 *A61N 1/08* (2006.01)
(52) U.S. Cl. .......................... 607/27; 607/28; 600/522; 600/901
(58) Field of Classification Search ................. 607/27, 607/28; 600/522, 901
 See application file for complete search history.

(56) References Cited

U.S. PATENT DOCUMENTS

| | | | |
|---|---|---|---|
| 4,549,548 A | 10/1985 | Wittkampf et al. | ... 128/419 PG |
| 5,545,183 A | 8/1996 | Altman | ........................... 607/5 |
| 5,707,398 A | 1/1998 | Lu | ............................... 607/27 |
| 6,085,118 A | 7/2000 | Hirschberg et al. | ............ 607/9 |
| 6,434,428 B1 | 8/2002 | Sloman et al. | ................ 607/28 |
| 6,477,417 B1 | 11/2002 | Levine | ........................... 607/9 |
| 6,788,971 B1 | 9/2004 | Sloman et al. | ................ 607/28 |
| 2004/0015197 A1 | 1/2004 | Gunderson | |
| 2004/0064161 A1* | 4/2004 | Gunderson et al. | ........... 607/28 |
| 2004/0088018 A1 | 5/2004 | Sawchuk et al. | ............. 607/27 |
| 2004/0106955 A1 | 6/2004 | Swerdlow et al. | |
| 2004/0220631 A1 | 11/2004 | Burnes et al. | |
| 2006/0074454 A1* | 4/2006 | Freeberg | ...................... 607/28 |

OTHER PUBLICATIONS

Gunderson, B. et al., "Ventricular Oversensing in ICD Patients: True Bipolar Versus Integrated Bipolar Sensing," *PACE*, vol. 24, p. 560 (Apr. 2001).
Kam, R. et al., "Transient Right Bundle Branch Block Causing R Wave Attenuation Postdefibrillation," *PACE*, vol. 20, Part 1, p. 130-1 (Jan. 1997).
Weretka, Slawomir, et. al., Ventricular Oversensing: A Study of 101 Patients Implanted with Dual Chamber Defibrillators and Two Different Lead Systems, PACE, vol. 26, 2003, pp. 65-70, XP002389354.

* cited by examiner

*Primary Examiner*—Carl Layno
*Assistant Examiner*—Yun Haeng Lee
(74) *Attorney, Agent, or Firm*—Michael C. Soldner; Girma Wolde-Michael

(57) ABSTRACT

An implantable cardioverter defibrillator (ICD) automatically determines whether to use electrogram (EGM) signals sensed by a true bipolar electrode pair or those sensed by an integrated bipolar electrode pair. EGM signals from both the true bipolar pair and the integrated bipolar pair are simultaneously sensed and compared to determine which pair produced more accurate sensing of cardiac events. The more accurate source of EGM signals is selected and used in determining the therapy to be delivered.

12 Claims, 4 Drawing Sheets

IMPLANTABLE CARDIOVERTER DEFIBRILLATOR WITH AUTOMATICALLY ADAPTABLE SENSING CONFIGURATION

BACKGROUND OF THE INVENTION

The present invention relates to implantable cardioverter defibrillators (ICDs), and more particularly to an ICD that automatically determines the most effective sensing electrode configuration.

An implantable cardioverter defibrillator provides therapies for maintaining and restoring normal cardiac rhythms by pacing or by delivering electrical shock therapy for cardioverting or defibrillating the heart. The ICD is implanted pectorally, and one or more electrical leads connected to the ICD are inserted into or in proximity to the heart of the patient. The leads carry current from the ICD to the heart tissue to stimulate the heart using either low energy pacing pulses or high energy cardioversion/defibrillation shocks. The leads are also used for sensing electrogram (EGM) signals from the heart that are used by the ICD to determine therapy to be delivered.

Within the ICD, sense amplifiers coupled to the leads amplify electrogram signals from the electrodes. The amplified EGM signal is filtered, rectified, and level-detected to sense intrinsic depolarizations of the atria (referred to as P-waves) and the ventricles (referred to as R-waves).

Single chamber ICDs use a single lead placed in the right ventricle to treat ventricular arrhythmia. Dual chamber ICDs treat ventricular arrhythmia (and in some cases atrial arrhythmia as well), and include one lead placed in the right ventricle and a second lead placed in the right atrium. In some cases, a third lead may be placed to gain access to the left ventricle (e.g. in the coronary sinus).

The ICD leads include a tip electrode that is attached to the wall or surface of the heart and a ring electrode that is located on the lead but spaced a short distance from the tip electrode. The ring and tip electrodes form a bipolar electrode pair for pacing and for sensing.

A high voltage coil used for delivering a cardioversion/defibrillation shock is also located on the ventricular lead. Some right ventricular leads carry two coils, one located in the right ventricle and the other located in the superior vena cava (SVC). A high voltage shock is typically applied between one of the high voltage coils and electrically conductive housing or can of the ICD.

The tip and ring electrodes of the lead are typically used for sensing EGM signals using a true bipolar sensing configuration. In some leads, the ring electrode is not present in order to reduce the number of conductors. In that case, the high voltage coil and the tip form an EGM sensing configuration which is referred to as integrated bipolar sensing. With improved lead technology, leads having a ring electrode, a tip electrode, and one or two high voltage coils are being used to a greater extent. These leads have the capability for both true bipolar sensing or integrated bipolar sensing. Current ICDs/leads provide for just one type of sensing.

For dual chamber detection algorithms in ICDs, based upon the sensed P-waves from the atrial lead and R-waves from the ventricular lead, the ICD delivers a therapy, which can include antitachycardia pacing (ATP), cardioversion or defibrillation. The effectiveness of the ICD in treating tachyarrhythmia depends upon the ability to accurately sense P-waves and R-waves with the atrial and ventricular leads, respectively. Oversensing of R-waves can produce an erroneous identification of ventricular tachycardia or fibrillation, resulting in unnecessary and painful cardioversion/defibrillation shocks and a waste of battery energy. Conversely, undersensing of R-waves can result in failure to detect ventricular tachycardia or fibrillation, and therefore failure to provide therapy when needed.

BRIEF SUMMARY OF THE INVENTION

In the present invention, an ICD simultaneously monitors EGM signals from true bipolar and integrated bipolar electrode sources. Based upon those signals, the ICD determines which electrode source provides more accurate sensing of cardiac events. The more accurate electrode source is used for future EGM sensing.

DETAILED DESCRIPTION

Figure 1:
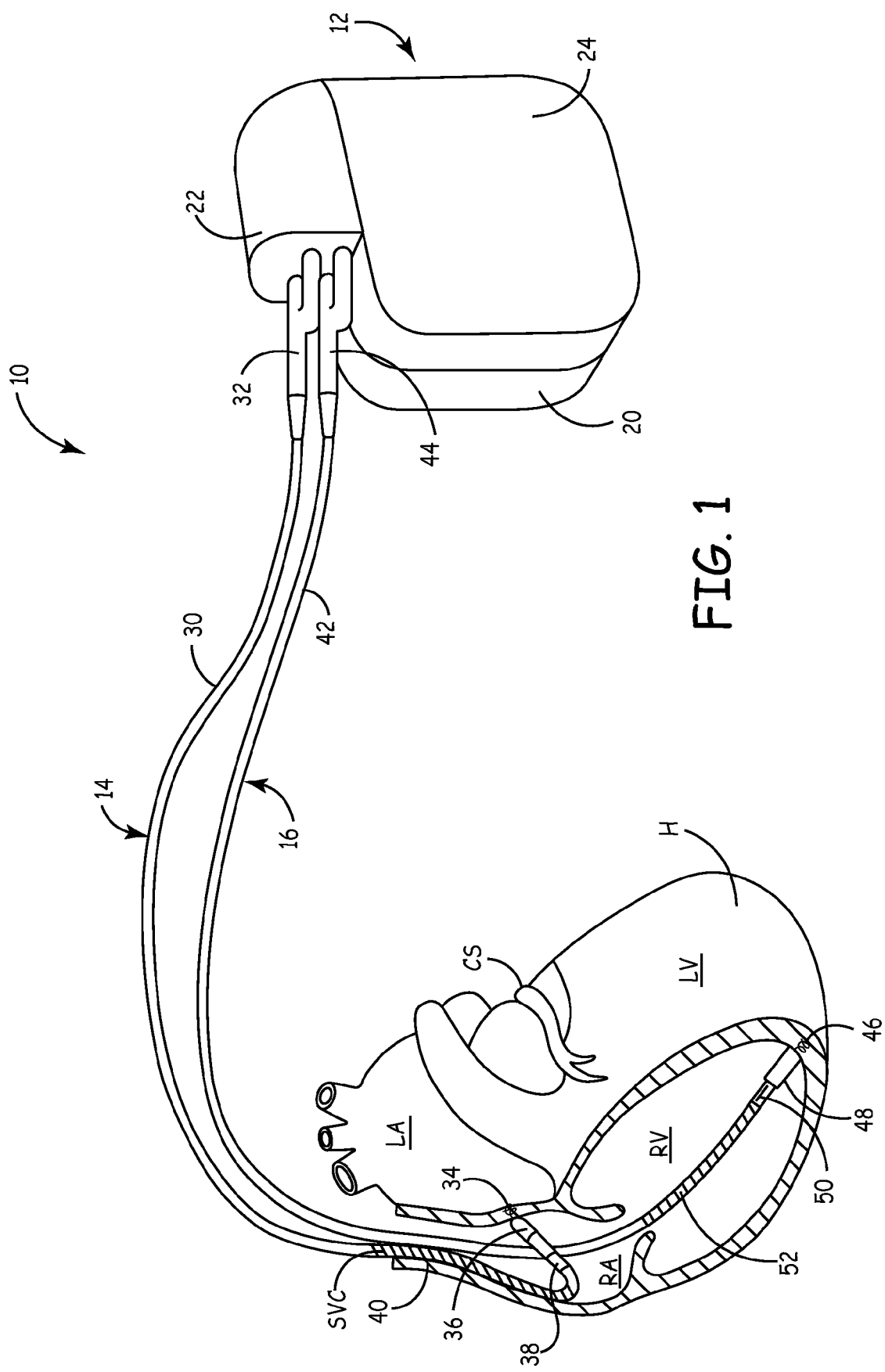
FIG. 1 is a diagram of an ICD and lead set of a type in which the present invention may be practiced.

FIG. 1 shows implantable medical device 10, which provides dual chamber pacing and cardioversion/defibrillation therapy to heart H. In FIG. 1, heart H is shown in a partially cutaway view illustrating right atrium RA, left atrium LA, right ventricle RV, left ventricle LV, coronary sinus CS, and superior vena cava SVC.

System 10 includes implantable cardioverter/defibrillator (ICD) 12, right atrial (RA) lead 14, and right ventricular (RV) lead 16. As shown in FIG. 1, ICD 12 includes housing or canister 20, header 22, and can electrode 24. The circuitry and power source of ICD 12 are located within housing 20. The circuitry communicates with leads 14 and 16 through electrical connectors within header 22. Can electrode 24 is formed on or is a part of the outer surface of housing 20, and acts as an electrode with respect to one or more of the electrodes carried by leads 14 and 16.

RA lead 14 is passed through the superior vena cava SVC into right atrium RA of heart H. RA lead 14 includes lead body 30, connector 32, distal tip attachment mechanism 34, tip electrode 36, ring electrode 38, and SVC coil electrode 40. Lead body 30 contains insulated conductors which extend from connector 32 to electrodes 36, 38, and 40. Connector 32 is a bifurcated connector that is inserted into connection bores within header 22 to provide electrical connection between electrodes 36, 38, and 40 and circuitry within ICD 12. Tip electrode 36 and ring electrode 38 are used to deliver pacing pulses to right atrium RA as well as to sense EGM signals within right atrium RA. Coil electrode 40 may be used to deliver a high voltage cardioversion or defibrillation pulse to superior vena cava SVC and right atrium RA. Can electrode 24 is used as the other electrode when a cardioversion/defibrillation pulse is delivered.

RV lead 16 is passed into right atrium RA, and then through the tricuspid valve into right ventricle RV. RV lead 16 includes lead body 42, connector 44, distal tip attachment mechanism 46, tip electrode 48, ring electrode 50, and coil electrode 52. In some embodiments, an SVC coil can be located on RV lead 16 rather than RA lead 14. Lead body 42 of RV lead 16 contains electrically insulated conductors which extend from connector 44 to tip electrode 48, ring electrode 50 and coil electrode 52. At the proximal end of RV lead 16, bifurcated connector 44 is inserted into a pair of connection bores of header 22 to provide electrical connection between the circuitry within housing 20 and electrodes 48, 50, and 52. Tip electrode 48 is placed in contact with the apex of right ventricle RV, and is fixed in place by attachment mechanism 46, which may be, for example, a screw or tined fastener.

Tip electrode 48 and ring electrode 50 form a true bipolar electrode pair which can be used for applying pacing pulses to right ventricle RV and sensing EGM signals representing electrical activity in right ventricle RV. Coil electrode 52 is used, in conjunction with can electrode 24 to apply high voltage cardioversion or defibrillation shock in order to halt ventricular arrhythmia. Together with tip electrode 48, coil electrode 52 also forms an integrated bipolar sensing electrode pair which can be used to sense EGM signals.

With the present invention, both the true bipolar electrode pair formed by tip electrode 48 and ring electrode 50 and the integrated bipolar sensor formed by tip electrode 48 and coil electrode 52 are monitored simultaneously by ICD 12. When there is a difference in the sensed R-waves using the two different EGM signals, ICD 12 evaluates the EGM signal having the greater number of detected R-waves (representing a higher ventricular rate) to determine whether the rate is higher due to known sources of oversensing. These include P-wave oversensing, T-wave oversensing, R-wave double counting, lead fracture/insulation break, electromagnetic interference, and myoelectric noise. If ICD 12 cannot positively identify a source of noise in the EGM signal producing the higher ventricular rate, then the sensor producing the slower rate is identified as undersensing. Based upon the evaluation, ICD 12 determines which of the two sensors is more accurately sensing R-waves, and selects that sensor as its source going forward. The simultaneous monitoring and comparison can continue after a switch from one source to the other has been made, so that a switch back is possible. Alternatively, only a single switch in source can be made, and only the chosen source is monitored thereafter.

Figure 2:
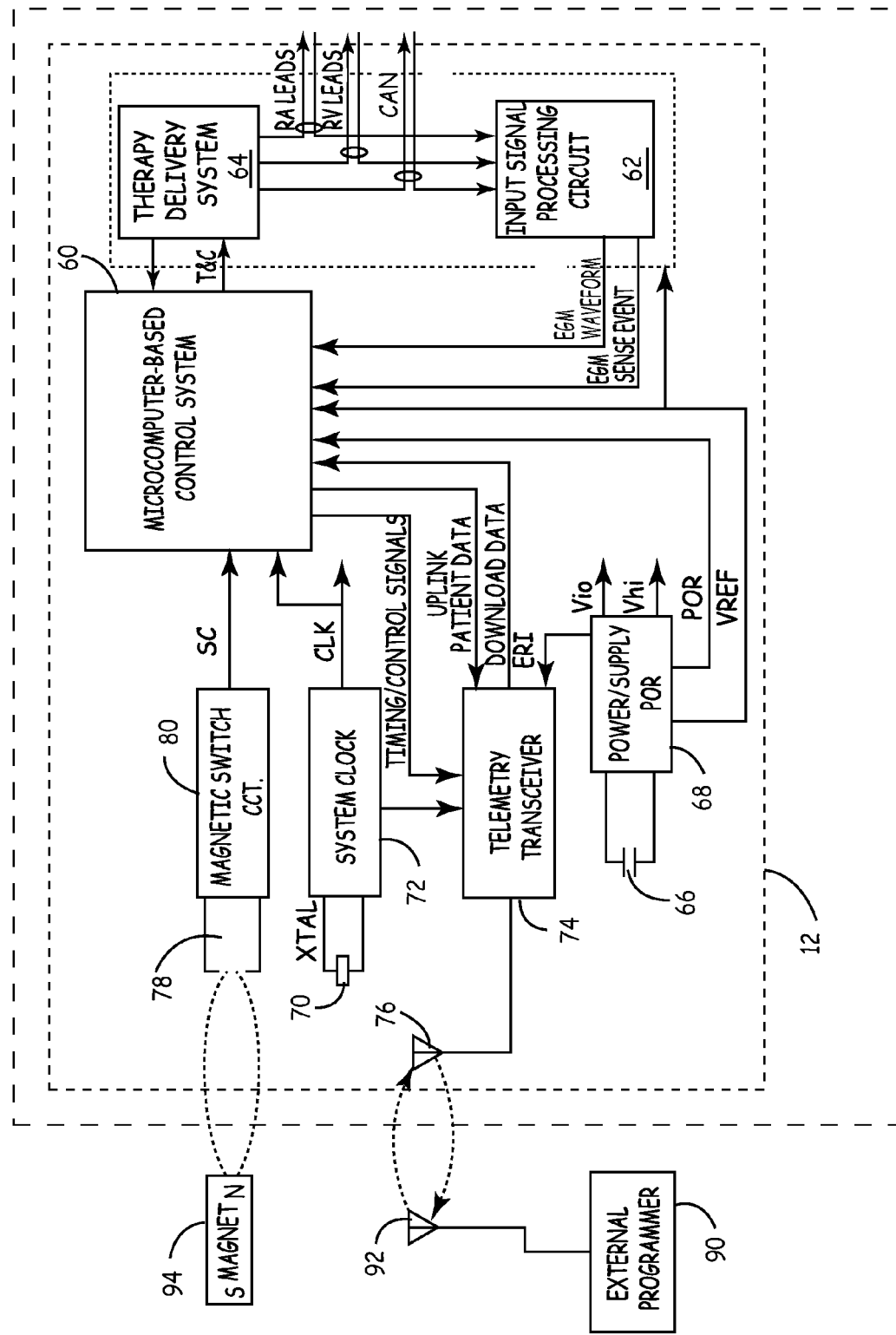
FIG. 2 is a block diagram of the ICD illustrated in FIG. 1.

FIG. 2 is an electrical block diagram of ICD 12 that provides delivery of therapy through leads 14 and 16 shown in FIG. 1. As shown in FIG. 2, ICD 12 includes microcomputer-based control system 60, input signal processing circuit 62, therapy delivery system 64, battery 66, power supply/power on reset (POR) 68, crystal oscillator 70, system clock 72, telemetry transceiver 74, antenna 76, switch 78, and magnetic switch circuit 80. Also shown in FIG. 2 are external programmer 90 and antenna 92 (which communicate with ICD 12 through antenna 76 and transceiver 74), and magnet 94 (which interacts with ICD 12 through switch 78 and magnetic switch circuit 80).

Control system 60 controls the functions of ICD 12 by executing firmware and program software algorithms stored in associated RAM and ROM. Control system 60 may also include additional circuitry including a watchdog circuit, a DMA controller, a block mover/reader, a CRC calculator, and other specific logic circuitry coupled together by an on-chip data bus, address bus, power, clock, and control signal lines. Control and timing functions can also be accomplished in whole or in part with dedicated circuit hardware or state machine logic rather than a programmed microcomputer.

Input signal processing circuit 62 receives signals from RA lead 14 and RV lead 16. The outputs of input signal processing circuit 62 include digitized EGM waveforms and sense event signals derived from the EGM signals sensed by leads 14 and 16.

Input signal processing circuit 62 includes a plurality of channels for sensing and processing cardiac signals from electrodes carried by leads 14 and 16. Each channel typically includes a sense amplifier for sensing specific cardiac events and an EGM amplifier for providing the EGM waveform signal to control system 60, where the EGM waveform is stored. In particular, separate channels are provided for the true bipolar sensing (tip electrode 48 and ring electrode 50) and the integrated bipolar sensing (tip electrode 48 and coil electrode 52) schemes of RV lead 16. This allows simultaneous monitoring and sensing of events (R-waves) using both sensing configurations. Input signal processing circuit 62 can be implemented with analog circuitry or with a digital signal processor.

Therapy delivery system 64 delivers cardiac pacing pulses to leads 14 and 16 under the control of control system 60. Delivery of pacing pulses is controlled in part by the selection of programmable pacing intervals, which can include atrial-atrial (A-A), atrial-ventricular (A-V) and ventricular-ventricular (V-V) intervals. Therapy delivery system 64 also includes circuitry for delivering cardioversion/ defibrillation therapy using SVC coil electrode 40, RV coil electrode 52 and can electrode 24.

Electrical energy for ICD 12 is supplied from battery 66 through power supply/power on reset (POR) circuit 68. This includes power to operate the circuitry controlling operation of ICD12, as well as electrical stimulation energy for delivery to heart H, and power for telemetry signal transmissions. Power supply/POR circuit 68 provides low voltage power Vlo, power on reset (POR) signal, reference voltage VREF, elective replacement indicator signal ERI and high voltage power Vhi (for cardioversion/defibrillator capabilities).

Clock signals for operation of the digital logic within ICD 12 are provided by crystal oscillator 70 and system clock 72. Control system 60 uses the clock signals for various time measurements, and produces timing and control signals based on the clock signals.

Uplink and downlink telemetry capabilities are provided through telemetry transceiver 74 and antenna 76. External programmer 90 can receive stored EGM data, as well as real-time generated physiologic data and nonphysiologic data from control system 60. In addition, programming data can be supplied from external programmer 90 to control system 60.

Magnetic field sensitive switch 78 and magnetic switch circuit 80, which issue a switch closed (SC) signal to control system 60 when magnet 94 is positioned over the subcutaneously implanted ICD 12. This indicates to ICD 12 that a communication device is present.

Figure 3:
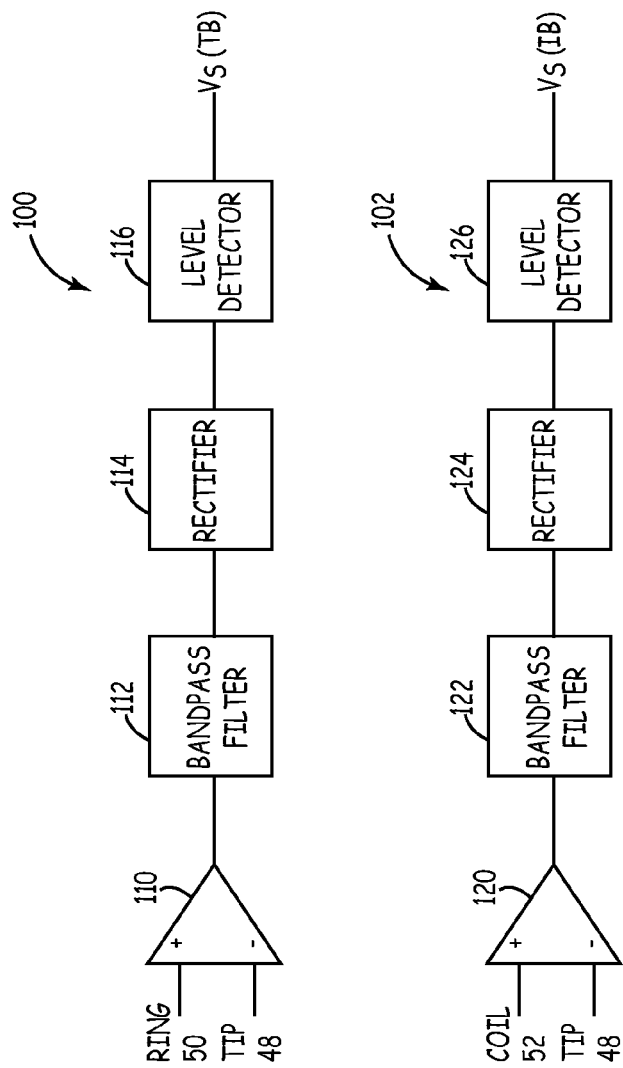
FIG. 3 is a block diagram showing EGM signal processing in the ICD.

FIG. 3 shows a functional diagram of signal processing channels 100 and 102, which form a part of input signal processing circuit 62. True bipolar channel 100 processes the true bipolar EGM signal from tip electrode 48 and ring electrode 50. Integrated bipolar channel 102 processes the integrated bipolar signal derived from tip electrode 48 and coil electrode 52.

True bipolar channel 100 includes differential amplifier 110, bandpass filter 112, rectifier 114, and level detector 116.

Integrated bipolar channel 102 includes differential amplifier 120, bandpass filter 122, rectifier 124, and level detector 126. Each channel 100 and 102 produces a V-sense signal $V_s$ in response to a detected R-wave representing a ventricular depolarization.

Ring electrode 50 and tip electrode 48 are closely spaced, similarly sized electrodes. Differential amplifier 110 provides an output representing the difference in potential between ring electrode 50 and tip electrode 48. This provides common mode rejection for potentials present simultaneously at both electrodes. After filtering by bandpass filter 112 and rectification by rectifier 114, the signal is compared to a sensing level by level detector 116, and a V-sense pulse is produced when the signal exceeds the sensitivity setting of level detector 116. The sensitivity setting should be set at a level so that every R-wave is detected, while P-waves (representing atrial depolarization), T-waves and other sources of electrical noise do not cause a V-sense signal to be produced.

Tip electrode 48 and coil electrode 52 are of different sizes and are based apart a further distance than ring electrode 50 and tip electrode 48. Differential amplifier 120 produces an output based upon the difference in potential between tip electrode 48 and coil electrode 52. That signal is filtered, rectified and compared to a sensitivity setting level to produce a V-sense signal from integrated bipolar channel 102.

In most instances, the outputs of channels 100 and 102 will be the same. However, there are circumstances where true bipolar sensing and integrated bipolar sensing may not provide the same R-wave sensing. It is important to proper ICD function that ventricular tachyarrhythmia is detected, so that proper therapy can be provided.

There are some circumstances under which true bipolar sensing can result in underdetection of R-waves. Integrated bipolar sensing, on the other hand, tends to have more oversensing issues due to T-wave oversensing, and can exhibit P-wave oversensing if the coil protrudes into or near the atrium.

Figure 4:
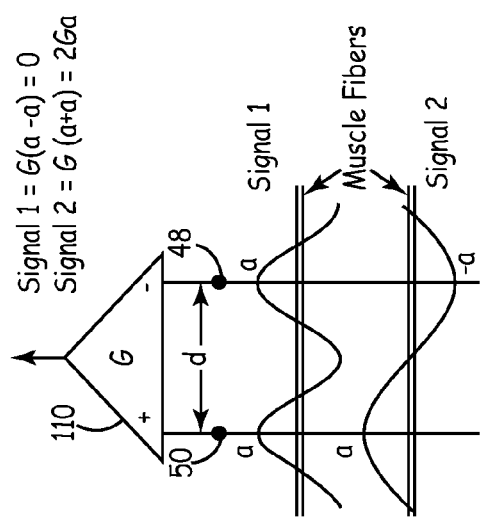
FIG. 4 is a diagram illustrating differential filtering with bipolar sensing.

Although inherently superior with respect to common mode rejection, true bipolar sensing is theoretically more apt to result in differential filtering and greater attenuation of the desired signal. This happens, for example, in a case where the depolarization wavefront is moving in a direction parallel to the bipole orientation established by tip and ring electrodes 48 and 50. FIG. 4 illustrates a differential filtering phenomenon. Signal 1 and Signal 2 are propagating through muscle fibers in a direction parallel to the bipole orientation. Both signals have the same peak-to-peak amplitude, but have different wavelengths. In the case of Signal 1, the wavelength of the signal is equal to NV/D, where N is an integer, V is conduction velocity, and D is the interelectrode distance between electrodes 48 and 50. Because electrodes 48 and 50 see the same signal amplitude from Signal 1 simultaneously, the output of differential amplifier 110 is zero in the case of Signal 1. Signal 2, on the other hand, has a wavelength which results in nonzero output from amplifier 110.

Figure 5A:
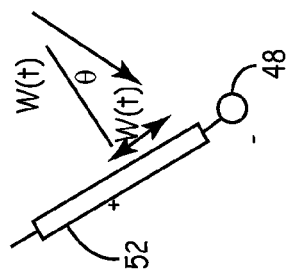
FIGS. 5A and 5B are diagrams illustrating differences in susceptibility to differential filtering to a wavefront represented by vector W(T) moving nearly perpendicular to a true bipolar (TB) and an integrated bipolar (IB) electrode configuration, respectively.
Figure 5B:
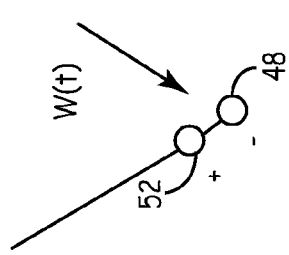

True bipolar sensing is also more susceptible to differential elimination of signals moving in a direction orthogonal to the bipole formed by tip electrode 48 and ring electrode 50. Integrated bipolar sensing between tip electrode 48 and coil electrode 52 is inherently less susceptible to differential elimination due to the difference in size of the two electrodes. FIGS. 5A and 5B demonstrate a situation where differential elimination is more complete with a true bipolar configuration versus an integrated bipolar configuration. In this representation, a wavefront represented by vector W(T) is shown moving nearly perpendicular to a true bipolar (TB) configuration in FIG. 5A and an integrated bipolar (IB) configuration in FIG. 5B. The resulting signal with the true bipolar configuration is likely to be near zero since electrodes 48 and 50 are closely spaced and of substantially the same size, and the wavefront will tend to reach both electrodes at about the same time. With the integrated bipolar configuration of FIG. 5B, the wavefront will vary according to the projection of W(T) according to cos Θ, where Θ is the angle between normal to coil electrode 52 and the direction of vector W(T).

Figure 6:
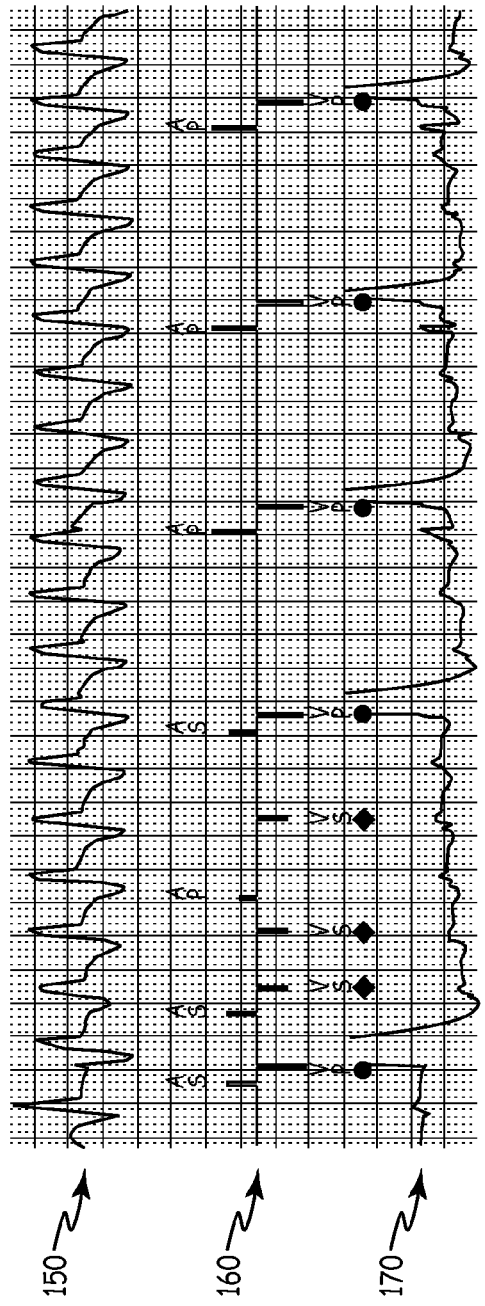
FIG. 6 is a graph illustrating an example of R-wave undersensing by a true bipolar electrode configuration.

FIG. 6 is a graph showing an example of undersensing of R-waves using a true bipolar differential sensing configuration in the case of a ventricular tachycardia having a right bundle branch block (RBBB) activation pattern. Top trace 150 is an ECG pattern. Center trace 160 shows atrial sense events and ventricular sense events. The ventricular sense events were based upon signal processing of the true bipolar EGM sensor signal shown in bottom trace 170. A comparison of the ECG pattern 150 with traces 160 and 170 shows that only a fraction of the R-waves were sensed.

With the present invention, channels 100 and 102 permit simultaneous monitoring of differentially filtered signals from true bipolar and integrated bipolar sensors. One of the two channels is initially selected as the primary channel. Typically this will be the true bipolar channel 100.

If the number of sensed events from the two channels is the same, then the results from the primary channel are used by control system 60. If, however, the number of sensed events over a period of time differs by greater than a preset value (e.g. greater than or equal to three), then the higher sense rate EGM signal is analyzed by control system 60 to see whether the higher sense rate is due to known sources of oversensing, such as P-wave oversensing, T-wave oversensing, R-wave double counting, lead fracture/insulation breaks, EMI, or muscle noise. The analyses may include checking for evidence of simultaneous sensing of both the atrial sensing and the ventricular sensing indicating P-wave oversensing, and the use of morphology analysis and comparison of stability of adjacent beats to identify T-wave oversensing. Other sources of noise can be detected using a short interval counter to identify intervals that are too short to have been produced by physiologic sources.

If control system 60 cannot positively identify a source of noise on the channel producing a higher sense rate, then it assumes that the lower sense rate EGM channel is undersensing. Control system 60 chooses the channel that represents the more reliable EGM source. Since the difference is likely to persist, control system 60 may decide to reject the channel that it has identified as being unreliable, and no longer continue to compare the results from the two channels.

With the present invention, the ICD has the ability to automatically determine the most accurate sensing electrode configuration and to select the better EGM source. This ability to automatically reconfigure to avoid undersensing or oversensing problems with a particular sensor avoids situations which might otherwise require a lead replacement or lead modification.

Although the present invention has been described with reference to preferred embodiments, workers skilled in the art will recognize that changes may be made in form and detail without departing from the spirit and scope of the invention.

The invention claimed is:

1. An implantable cardioverter defibrillator (ICD) comprising:
    a lead having a plurality of electrodes for providing a first EGM signal and a second EGM signal;
    a first signal processing channel for producing a first set of sense signals based on the first EGM signal;
    a second signal processing channel for producing a second set of sense signals based on the second EGM signal;
    a therapy delivery circuit for providing an electrical therapy through the lead based on one of the first and second sets of sense signals; and
    a control unit for analyzing the first and second sets of sense signals and the first and second EGM signals and selecting the set of sense signals used by the therapy delivery circuit.

2. The ICD of claim 1 wherein the control unit analyzes, for oversensing, the EGM signal corresponding to the set producing a greater number of sensing signals.

3. The ICD of claim 2 wherein the control unit selects the set producing a greater number of sense signals if analysis of the EGM signal does not identify instances of oversensing.

4. The ICD of claim 1 wherein the first and second signal processing channels include analog signal processors.

5. The ICD of claim 1 wherein the first and second signal processing channels include digital signal processors.

6. The ICD of claim 1 wherein the first EGM signal is a true bipolar (TB) sensing signal and the second EGM signal is an integrated bipolar (IB) sensing signal.

7. The ICD of claim 6, wherein the control unit:
    selects the TB sensing signal if both the TB sensing signal and the IB sensing produce similar sensing of cardiac events or the IB sensing signal exhibits oversensing; and
    selects the IB sensing signal if the TB sensing signal exhibits undersensing.

8. An implantable cardioverter defibrillator (ICD) comprising:
    a lead having a tip electrode, a ring electrode, and a coil electrode;
    a true bipolar (TB) sensing circuit for delivering a true bipolar sensing signal from the tip electrode and the ring electrode;
    an integrated bipolar (IB) sensing circuit for deriving an integrated bipolar sensing signal from the tip electrode and the coil electrode;
    a control unit that compares the TB sensing signal and the IB sensing signal and selects one of the TB and IB sensing signals as a basis for therapy; and
    a therapy delivery circuit for delivering therapy through at least one of the electrodes based on the sensing signal selected wherein the control unit compares numbers of sensed events by the TB sensing signal and the IB sensing signal.

9. The ICD of claim 8 wherein the control unit selects the signal with more sensed events unless the control determines that oversensing has occurred.

10. The ICD of claim 8, wherein the control unit:
    selects the TB sensing signal if both the TB sensing signal and the IB sensing signal produce similar sensing of cardiac events or the IB sensing signal exhibits oversensing; and
    selects the IB sensing signal if the TB sensing signal exhibits undersensing.

11. The ICD of claim 8 wherein the TB sensing circuit and the IB sensing circuit include analog signal processors.

12. The ICD of claim 8 wherein the IB sensing circuit and the IB sensing circuit include digital signal processors.

* * * * *